United States Patent [19]

Agee et al.

[11] Patent Number: 4,964,861

[45] Date of Patent: Oct. 23, 1990

[54] INSTRUMENTATION FOR IMPLANTING PROSTHETIC DEVICES

[75] Inventors: John M. Agee, 77 Scripps Dr., #101, Sacramento, Calif. 95825; Francis C. King, Sacramento, Calif.

[73] Assignee: John M. Agee, Sacramento, Calif.

[21] Appl. No.: 289,013

[22] Filed: Dec. 22, 1988

[51] Int. Cl.$^5$ .................. A61B 17/00; A61F 2/30; A61F 2/42

[52] U.S. Cl. .................. 606/87; 606/96; 606/97; 623/18; 623/21; 40/367

[58] Field of Search .................. 623/18, 21, 16, 20, 623/22, 23; 606/53, 79, 82, 86–89, 96–99, 102

[56] References Cited

U.S. PATENT DOCUMENTS 4,621,630 11/1986 Kenna .................. 606/89
4,757,810 7/1988 Reese .................. 606/87 X Primary Examiner—Ronald Frinks
Attorney, Agent, or Firm—Dean P. Edmundson

[57] ABSTRACT

Instrumentation is described for facilitating implantation of prosthetic devices in metacarpal bones, for example. Various embodiments are disclosed which include (a) means for determining the proper orientation of the prosthetic devices, and (b) means for defining the angle and location at which each metacarpal bone is cut in order to receive the prosthetic device.

26 Claims, 9 Drawing Sheets

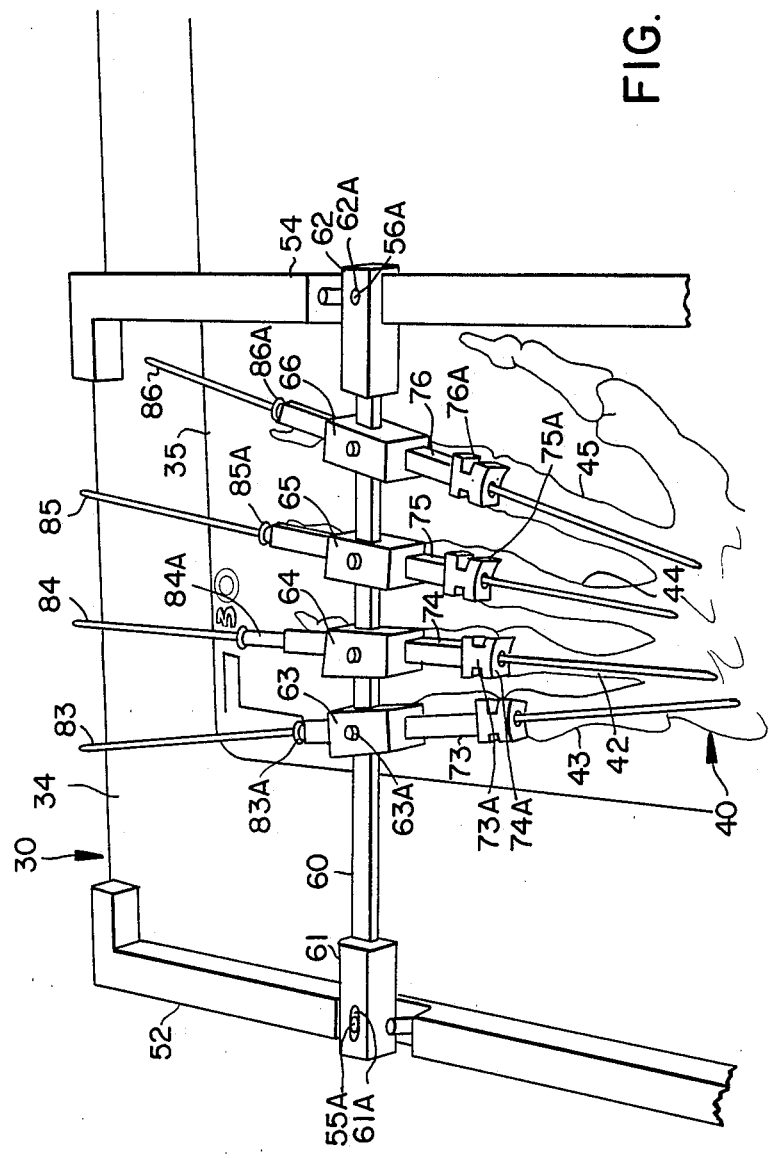

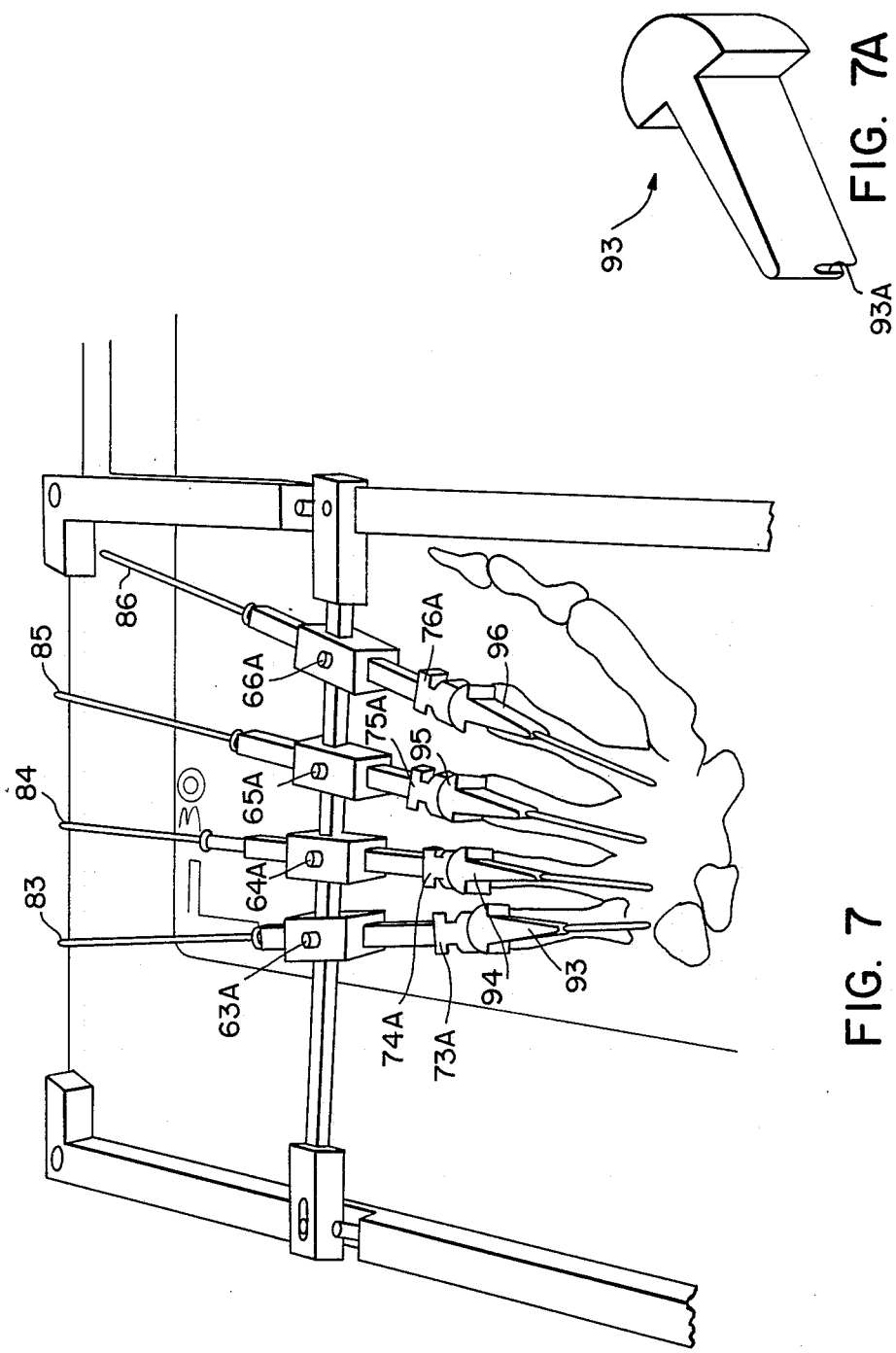

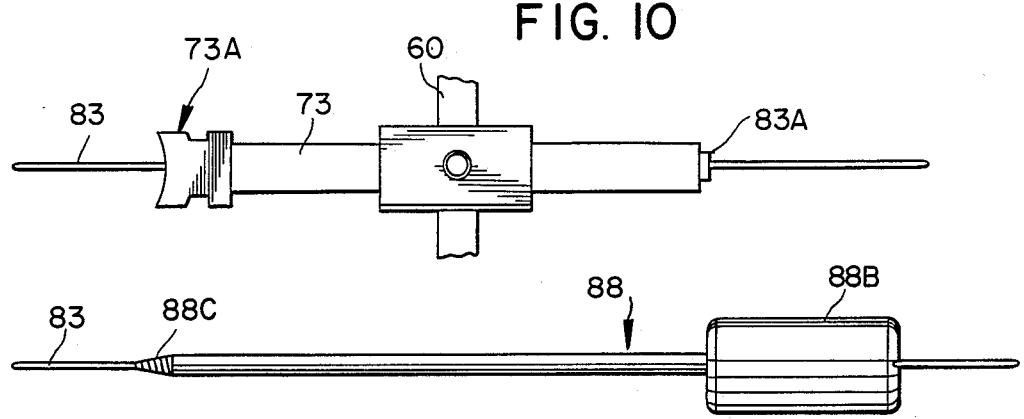
FIG. 10
FIG. 11
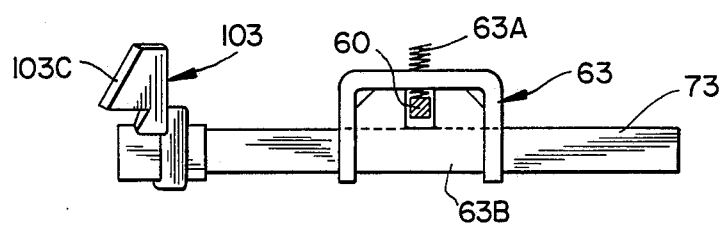
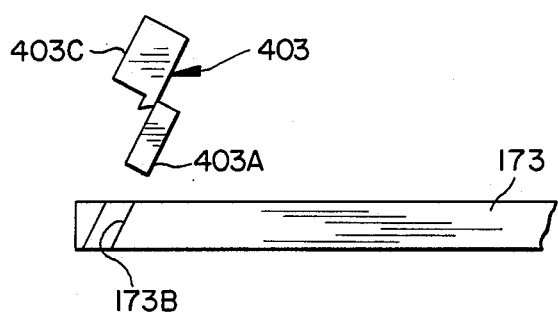
FIG. 9
FIG. 13

INSTRUMENTATION FOR IMPLANTING PROSTHETIC DEVICES

FIELD OF THE INVENTION

This invention relates to implantation of prosthetic devices. More particularly, this invention relates to instrumentation, processes and techniques for implanting prosthetic devices. Even more particularly, this invention relates to instrumentation and techniques for determining proper location, the angle, and the quantity or degree of resection of bone in which a prosthetic device is to be implanted in a patient.

BACKGROUND OF THE INVENTION

Prosthetic devices of various types have proven very useful in restoring function and mobility in patients. Many of such prosthetic devices are the type which are intended for implantation in the body, e.g., joints. In such circumstances it is necessary for the devices to be secured to bone structure in some manner.

Particular prosthetic devices which are useful as joints in the human body are described in U.S. Pat. No. 4,349,922, incorporated herein by reference. Although such devices are useful as joints in the wrist and hand, they are especially useful as joints between a metacarpal bone and a proximal phalanx (i.e., the metacarpophalangeal joint).

The prosthetic devices of the type just referred to include two portions which are pivotably and rotationally coupled together so as to enable relatively normal movement of the fingers of the hand after implantation. Each of the two portions of the prosthetic device includes an elongated stem member which is adapted to be inserted into and anchored within separate bone structure in the body, as described and taught in the aforementioned patent.

The prosthetic devices referred to above are especially useful in replacing the normal joint between the metacarpal bone and proximal phalanx of persons afflicted with severe arthritis, particularly rheumatoid arthritis in which there are advancing degrees of destruction of the articular joint surfaces associated with erosion of the bone and attenuation of the collateral ligaments with secondary subluxation or dislocation of the base of the proximal phalanx on the metacarpal head. In such cases it is often necessary to replace more than one, and often four, of the metacarpal phalangeal joints of the fingers in one operation because of the progression and extent of the disease.

For this type of surgery it is necessary to use a tourniquet to prevent blood loss while the prosthetic devices are being implanted. However, use of a tourniquet in this situation should typically be limited to no more than two hours in order to help avoid complications secondary to tissue ischemia. Therefore, it is advantageous to complete the implantation of the prosthetic devices within a two-hour period. Otherwise additional tourniquet times will be required. This, of course, requires extension of the anesthetic time, all of which relatively increases the risks to the patient.

Therefore, when there are multiple devices to be implanted in a given hand it is extremely desirable to have refined instrumentation which is able to facilitate the proper resection of arthritic bones at the appropriate angles to assure proper implantation of the prosthetic devices relative to the long axes of the bones with due respect for the angles of resection such that the installed metacarpophalangeal joints will allow flexion and extension of adjacent fingers to occur along parallel planes in space. This assures that the fingers will not be mal-rotated or cross over each other during flexion and extension.

In order to obtain the proper orientation of the prosthetic device with respect to the metacarpal bone, the head of the bone must be resected in a defined manner so that it is complementary to the apposed portion of the prosthetic device to be implanted in such bone. It is difficult to assuredly and reproducibly obtain the proper orientation of the prosthetic device(s) by simple visual observation.

There has not heretofore been provided instrumentation to assist in providing and controlling proper orientation of metacarpophalangeal joint prosthetic devices of the type described herein. Further, there have not previously been provided processes or techniques for efficiently and effectively assisting a surgeon in determining and obtaining proper resection of bone structure in which this type of prosthetic device is to be implanted.

SUMMARY OF THE PRESENT INVENTION

In accordance with the present invention there is provided instrumentation for determining and controlling proper orientation of one or several prosthetic devices intended for implantation in bone structure of a patient. In one embodiment the instrumentation comprises:

(a) support means for pre-operatively positioning guide apparatus to fit the unique anatomy of the patient's hand or other appropriate bone structure in which the prosthetic device is to be implanted;

(b) orientation means for defining a surface to be cut in the bone structure;

(c) alignment means carried by the support means for aligning the orientation means with the bone.

In another more preferred embodiment the instrumentation comprises:

(a) a transverse support and alignment member;

(b) a mounting block carried on the support member; the mounting block being movably adjustable along the longitudinal axis of the support member;

(c) an elongated bar carried by the mounting block, the bar being movably adjustable in a longitudinal direction on the mounting block; wherein the bar includes a longitudinal bore therethrough; wherein the bar further includes a head portion at one end thereof;

(d) a rod member slidably received in the longitudinal bore and being longitudinally movable therein; and (e) orientation means carried by the head portion for defining a surface to be cut in the bone.

Preferably the instrumentation described above is adapted to be retained in a frame carried by an x-ray viewer having a light source and a viewing surface for supporting an x-ray. An x-ray of the bone structure in which the prosthetic device is to be implanted is supported on the viewing surface and aligned with a reference point and a reference line. Then the instrumentation is properly aligned with respect to the metacarpal bones shown on the x-ray such that the angular orientation of the instrumentation and the dimensional spacing of one metacarpal from the others, and the position of each metacarpal head is set with respect to the instrumentation, after which the instrumentation is locked or secured in a set position for later use during surgery.

During surgery to implant the prosthetic device(s) the instrumentation is secured to the relevant bone structure of the patient in a manner such that the proper location and orientation are defined for resecting the bone structure which is to receive the prosthetic device(s).

With the use of the instrumentation and the techniques provided by the present invention the surgeon is able to effectively and efficiently prepare bone structure for implantation, and due to the efficiency of the techniques and procedure described herein, the instrumentation minimizes the time required for the bone resection portion of the operative procedure. Thus, the instrumentation and techniques described herein allow for implantation, and due to the efficiency of the techniques and procedure described herein, the instrumentation minimizes the time required for the bone resection portion of the operative procedure. Thus, the instrumentation and techniques described herein allow for implantation of one or more prosthetic devices within the time allowed for safe surgical procedures. Also, use of the instrumentation described herein assures that the prosthetic device will properly fit the bone structure of the patient.

The instrumentation and techniques provided by this invention allow for one or more (e.g., four) prosthetic devices to be implanted in a given hand by a method which references each of the prosthetic devices to the ring finger metacarpal bone. This is the thinnest or most narrow metacarpal bone. By referencing each prosthetic device to the ring finger metacarpal bone, the surgeon is assured that proper orientation and implantation of the prosthetic devices in the other metacarpal bones of the hand will be achieved. Then if it becomes necessary to implant a prosthetic device in the ring finger metacarpal bone the surgeon will be assured that the prosthetic device implanted in such bone will be properly aligned in a plane parallel to the plane of motion of the adjacent previously reconstructed joints.

The instrumentation of this invention is also unique in that it includes means allowing it be to adapted for use on each patient in an individual manner unique to that patient. Also, the instrumentation enables each finger of a given hand to be separately and properly prepared for implantation of an MP joint.

The instrumentation also controls the proper angle of orientation of each MP joint relative to the corresponding metacarpal bone. The instrumentation enables the surgeon to plan for implantation of one or more MP joints by prealigning the instrumentation to a pre-operative X-ray of the hand. The surgeon is able to readily adjust the instrumentation for the position of the metacarpal bones relative to each other, and the surgeon can also readily adjust the instrumentation for the relative length of each metacarpal bone.

Other advantages of the instrumentation and techniques of the present invention will become apparent from the following detailed description and the accompanying drawings.

BRIEF DESCRIPTION OF THE DRAWINGS

The invention is described in more detail hereinafter with reference to the accompanying drawings, wherein like reference characters refer to the same parts throughout the several views and in which:

FIG. 6 illustrates the instrumentation of the invention retained on the fixturing apparatus of FIGS. 4 and 5 with an x-ray on the viewing surface of the fixturing apparatus;

FIG. 7 illustrates the instrumentation of FIG. 6 and the manner in which the proper size prosthetic device is selected for implantation;

FIG. 7A illustrates another type of aid which may be used to assist in selecting the proper size of prosthetic device for a particular patient;

FIG. 9 is a side elevational view of one of the elongated arms (metacarpal axis arm) shown in FIG. 8;

FIG. 10 is a top view of the elongated arm shown in FIG. 9 with the orientation head means removed and a K-wire and sleeve inserted into the longitudinal bore of the elongated arm;

FIG. 11 illustrates a threaded tool with a K-wire inserted in a longitudinal bore through the tool;

FIG. 13C is a side elevational view illustrating another manner in which an orientation head member may be attached to the end of a metacarpal axis arm;

DETAILED DESCRIPTION OF THE INVENTION

Figure 1:
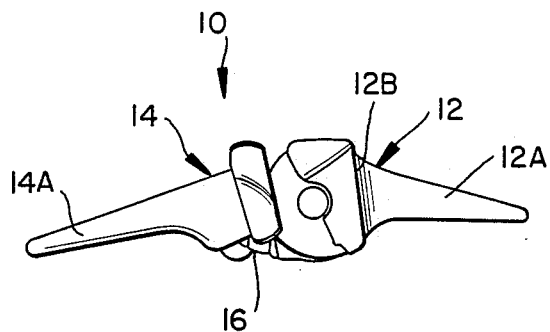
FIGS. 1 and 2 illustrate a prosthetic device for total replacement of a metacarpophalangeal joint of a human finger.
Figure 2:
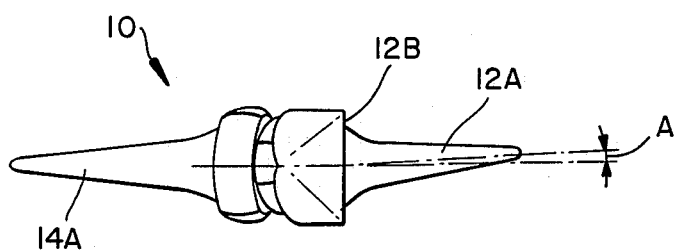

In FIGS. 1 and 2 there is illustrated a preferred type of prosthetic device 10 comprising a metacarpophalangeal joint (MP joint) which is useful as an implant in the hand of a patient having advanced arthritis, for example. The device comprises portion 12 and portion 14 which are coupled together by means of pin 16 in a manner such that the two portions may pivot and rotate slightly with respect to each other (i.e., to simulate the movement of a normal biological MP joint in the hand).

Portion 12 includes an elongated stem member 12A which projects or extends outwardly from rear face 12B, as illustrated. Portion 14 includes an elongated stem member 14A which projects or extends outwardly, as illustrated.

In the particular device shown in FIGS. 1 and 2 the stem member 12A is offset slightly so that the central axis of stem 12A forms an angle A with respect to an imaginary line which is perpendicular to face 12B. The offset angle is highly desirable because each phalanx or finger connects to a respective metacarpal bone at an angle. In other words, the longitudinal central axis of each phalanx or finger is not in parallel alignment with the longitudinal central axis of its respective metacarpal bone.

Although there is some variation from one person to another, it has been found that the little finger and the index finger normally are offset at an angle of about 11° from the longitudinal centerline of the hand while the ring finger and middle finger normally are offset at an angle of about 4° from the longitudinal centerline of the hand.

Figure 6A:
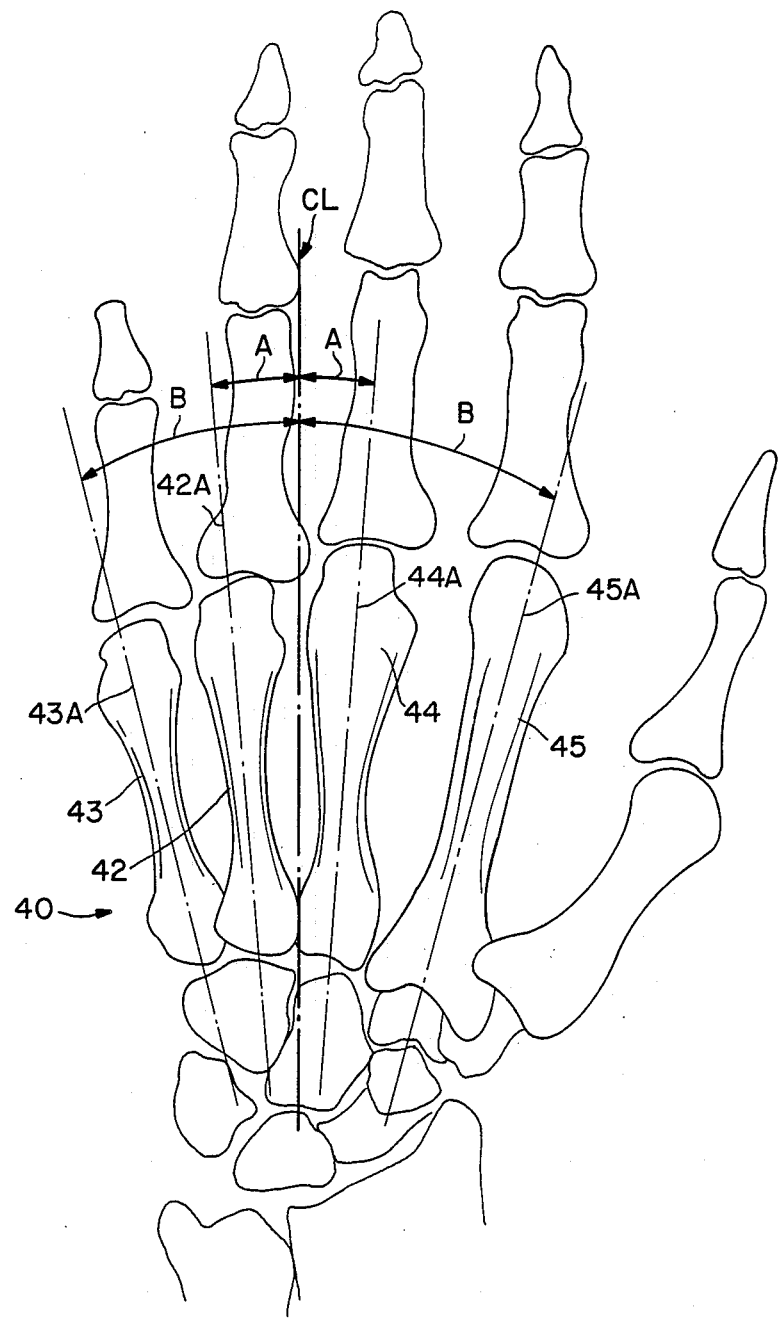
FIG. 6A illustrates the centerline of a human hand.

FIG. 6A illustrates an X-ray of a human hand 40 which includes metacarpal bones 43, 42, 44 and 45 from little finger to index finger. The centerline CL of the hand is shown with bold line.

The angle A formed between centerline CL and the central longitudinal axis 42A of metacarpal bone 42 is generally and normally about 4°. Similarly, the angle A formed between centerline CL and the central longitudinal axis 44A of metacarpal bone 44 is generally and normally about 4°.

The angle B formed between centerline CL and the central longitudinal axis 43A of metacarpal bone 43 is generally and normally about 11°. Similarly, the angle B formed between centerline CL and the central longitudinal axis 45A of metacarpal bone 45 is generally and normally about 11°.

The stem member 12A of prosthetic device 10 is intended for insertion into the hollow or medulla of a metacarpal bone, after the head of the metacarpal bone has been resected. The stem member 14A of the device is intended for insertion into the hollow or medullary canal of a proximal phalanx.

The stem members are cemented or grouted in place in conventional manner. For example, a cement comprising polymethylmethacrylate may be used effectively. Other means for securing the stem members in place may also be used.

Figure 3:
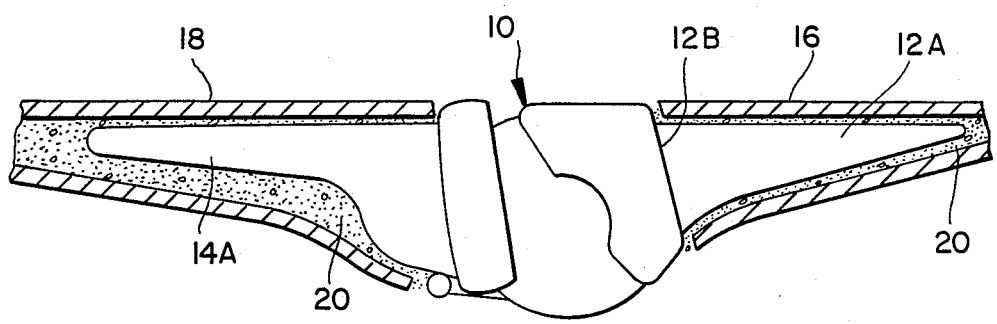
FIG. 3 is a side view, partially cut-away, showing the prosthetic device implanted in a hand, with one end or stem of the device being secured in a metacarpal bone (typically with bone cement or grouting agent) and the other end or stem being secured in a proximal phalanx.

FIG. 3 is a side elevational, partially cut-away view illustrating a prosthetic device 10 implanted in a hand between metacarpal bone 16 and proximal phalanx 18, as illustrated. Grouting 20 secures or anchors each stem in the hollow or canal of the respective bones.

As illustrated in FIG. 3, the head of metacarpal bone 16 has been resected at an angle which is parallel to the rear face 12B of prosthetic device 10. The rear face 12B is sloped, and the distal end of metacarpal bone 16 is resected at the same angle so that rotation of the prosthetic device relative to the metacarpal bone is further restricted. This adds additional strength and durability to the joint. Normally only a portion of the head is resected so that as much of the metaphyseal flare as possible remains for biologic and biomechanical purposes.

Figure 4:
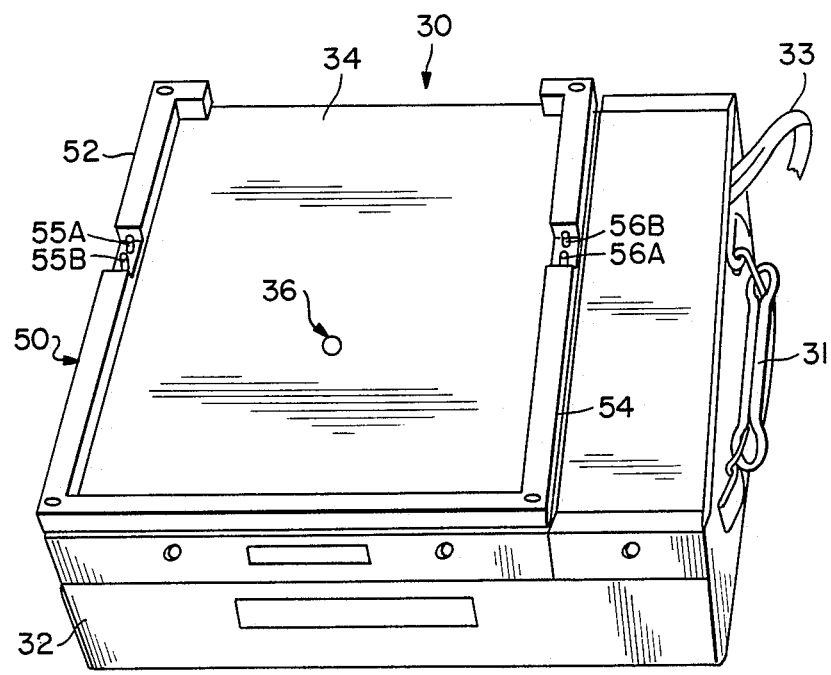
FIGS. 4 and 5 are perspective views of fixturing apparatus containing an X-ray view box for facilitating proper orientation of instrumentation with an x-ray of bone structure.
Figure 5:
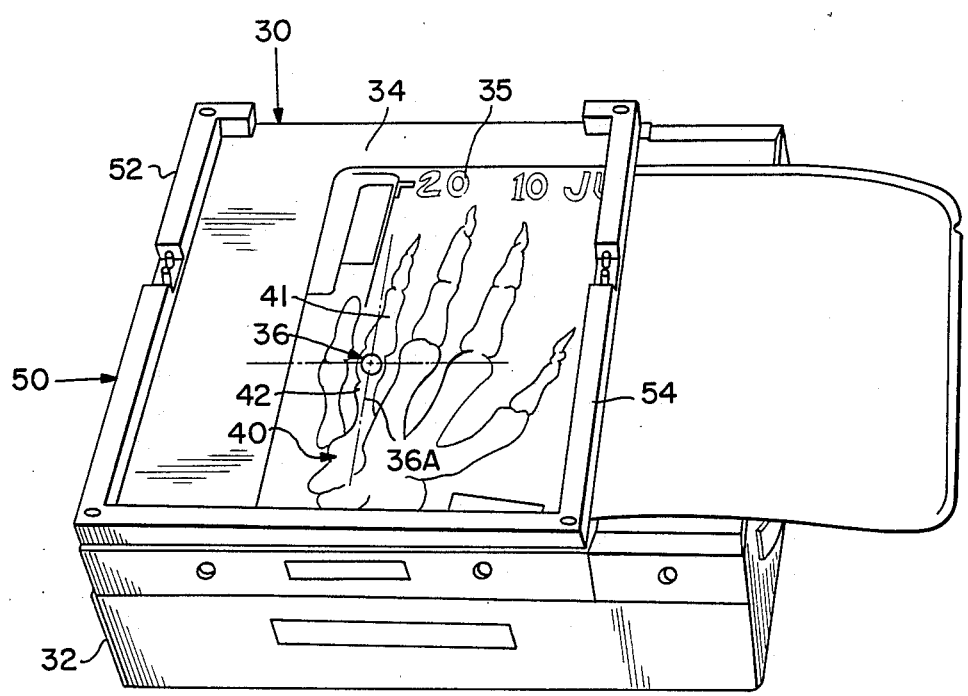

FIGS. 4 and 5 illustrate an x-ray viewing box or device 30 and fixture which is very useful in the practice of this invention. The device comprises housing or enclosure 32 which is generally rectangular in shape and includes a planar x-ray viewing surface 34 and a light source (not shown) within the housing. For example, surface 34 may comprise a conventional translucent plastic member which allows light to pass through it from the light source so as to facilitate viewing of an x-ray film 35. Power cord 33 is operably connected at one end to the light source within the housing and is adapted to be connected at its opposite end to a conventional power source. Handle member 31 may be included in order to facilitate carrying of the viewer.

Viewing surface 34 includes reference means 36 comprising cross-hairs and a circle. The reference means is used as illustrated in FIG. 5 in order to properly align the x-ray film on the viewing surface. As shown, the top of the circle is aligned with the head of the metacarpal bone 42 which corresponds to the ring finger 41 of hand 40. The lower vertical cross-hair 36A is aligned with the central longitudinal axis of metacarpal bone 42 corresponding to the ring finger.

Viewer 30 also preferably includes frame means 50 having side members 52 and 54. Side member 52 includes posts 55A and B, and side member 54 includes posts 56A and B. If desired, frame means 50 may be hinged to viewer 30 to facilitate insertion and removal of an x-ray film from viewing surface 34. Alternatively, the frame means could include notches or openings therein for registration with upstanding pegs or pins on viewing surface 34.

FIG. 6 illustrates use of instrumentation apparatus of the invention in connection with viewing device 30. The instrumentation includes an elongated transverse support member 60 having ends 61 and 62. End 61 includes a slotted aperture 61A and end 62 includes a round aperture 62A.

In FIG. 6 the slot 61A is positioned over post 55A on frame section 52 and aperture 62A is positioned over post 56A on frame section 54. This orientation of transverse support member 60 is used when a left hand x-ray 35 is on the viewing surface 34. When an x-ray of a right hand is on the viewing surface, end 61 of support member 60 is positioned over post 55B and end 62 is positioned over post 56B.

Mounting blocks 63, 64, 65 and 66 are carried on support member 60, as illustrated. Each mounting block carries an elongated bar 73, 74, 75 and 76, respectively, corresponding to the metacarpal bones 43, 42, 44 and 45 of the hand 40.

Each elongated bar includes a longitudinal bore therethrough in which a sleeve member 83A, 84A, 85A, and 86A, respectively, is slidably received. A K-wire 83, 84, 85 and 86, respectively, is slidably inserted through each respective sleeve member. A K-wire is a Kerschner wire which is well known. It is a stainless steel rod having a diameter of about 0.62 inch.

Each mounting block is longitudinally movable on support member 60 in a manner such that the K-wire can be closely aligned with the longitudinal central axis of a respective metacarpal bone. Each elongated bar is adjustably movable in a longitudinal manner such that the concave leading surface of the head portion (73A, 74A, 75A, and 76A, respectively) can be aligned with the distal end of a respective metacarpal bone on the x-ray.

The angle of each mounting block with respect to the transverse support member 60 is preferably predetermined. In other words, corresponding metacarpal bones of a wide cross-section of the human population generally form similar angles with respect to the longitudinal centerline of the hand as illustrated in FIG. 6A. As a result, by averaging the slight variance in these angles it has been found possible to predetermine a suitable angle with respect to each metacarpal bone in the hand, which angle is then determinative of the standard orientation for each mounting block and elongated bar with respect to transverse support member 60.

Thus, in a preferred embodiment each mounting block and associated elongated bar is held at a fixed, predetermined angle with respect to transverse support member 60. Each mounting block may be adjustably moved longitudinally along the support member, and the associated elongated bar may be adjustably moved in a longitudinal direction corresponding to its own longitudinal axis, but the angle with respect to support member 60 is preferably pre-set. A threaded set screw such as 63A then is used to secure each mounting block on support member 60 at any desired position.

Each mounting block is rotationally fixed on the support member 60. In other words, each mounting block can be loosened and moved along the length of the support member 60 but the mounting block is prevented from rotating relative to support member 60.

After the head portion of each elongated rod is properly aligned with the head of a respective metacarpal bone and then secured in position, a sizing aid or template is slipped over the K-wire and laid on top of the corresponding metacarpal bone on the x-ray. This is illustrated in Figure 7 where aids 93, 94, 95 and 96 are slipped onto K-wires 83, 84, 85 and 86, respectively.

The head of each sizing aid or template is rounded, as illustrated, so that it will fit in the concave area of the head portion of a corresponding elongated bar. The sizing aids also include a stem portion, as shown. The sizing aid may include a longitudinal bore so that it can slidably engage a respective K-wire, as shown in FIG. 7. Alternatively, the aid may include a longitudinal slot or groove 93A on its underside (as illustrated in FIG. 7A) so that the aid can be more quickly and easily set over a respective K-wire.

The sizing aids are provided in different sizes to correspond with the available sizes of pre-manufactured prosthetic devices. For example, there may be four or more separate sizes of prosthetic devices manufactured. A sizing aid corresponding to each such device (in size and shape) is available for use as illustrated in FIG. 7 in order to facilitate selection of the properly sized prosthetic device for implantation. This also helps in a determination of how much of the metacarpal bone is to be resected.

Figure 8:
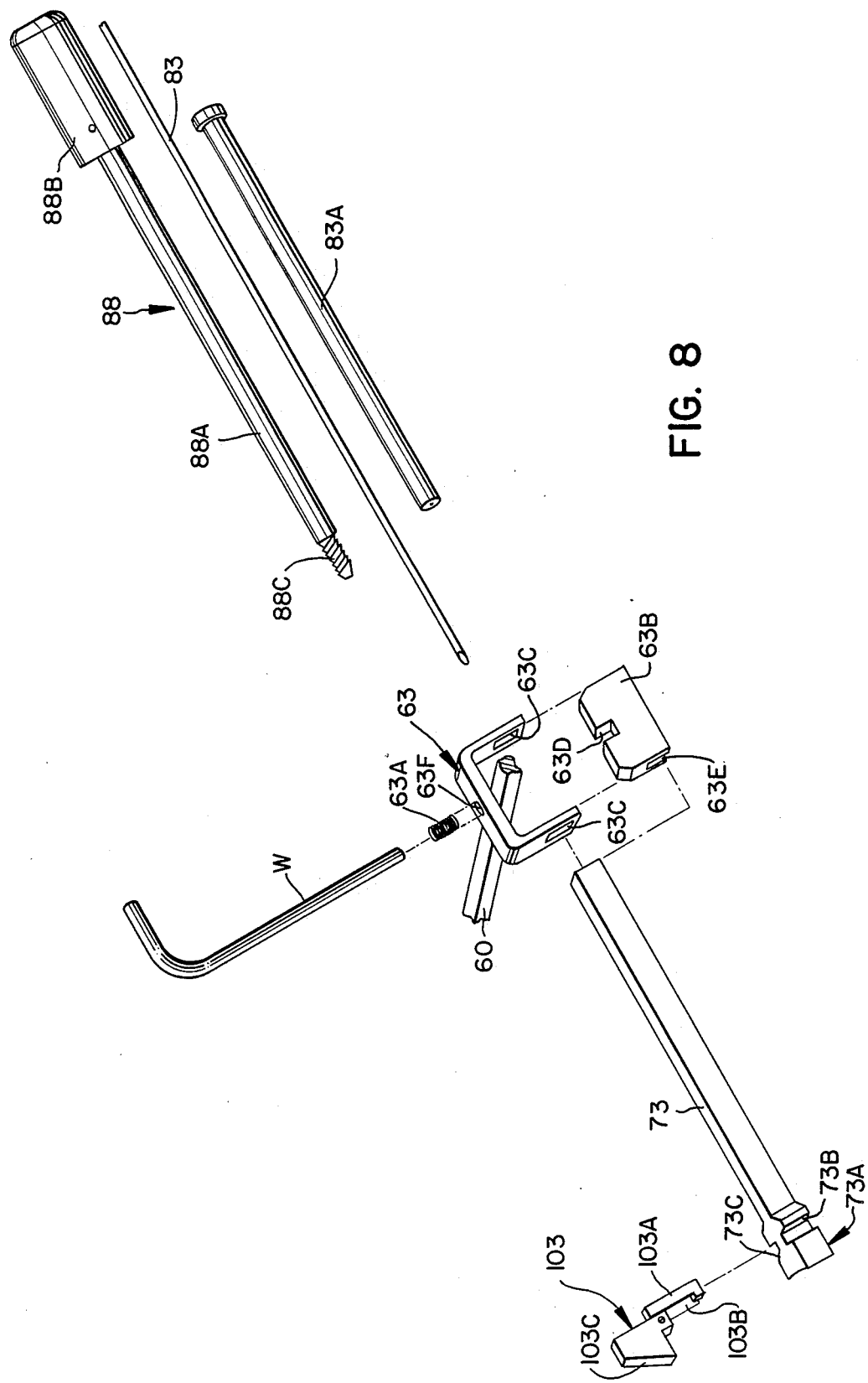
FIG. 8 is an exploded view illustrating certain components of the instrumentation useful in the present invention.

FIG. 8 is an exploded view illustrating the preferred manner in which one such elongated bar 73 is secured to transverse support member 60. The mounting block 63 includes a U-shaped member having openings 63C in the depending leg portions to slidably receive bar 73. Set screw 63A is adapted to threadably engage opening 63F extending through the top portion of the U-shaped member. Wrench W may be used for this purpose.

Block member 63B includes a longitudinal slot 63E in its underside in which bar 73 is received when block 63B is positioned within the U-shaped member. Block 63B also includes a transverse slot 63D in its top surface to receive support member 60. If desired, slot 63D may extend down to intersect longitudinal slot 63E. In such event, the support member 60 will rest upon the top surface of bar 73. By tightening set screw 63A the bar 73 is secured relative to support member 60. The angle of slot 63D in block 63B determines the angle of bar 73 relative to support member 60.

Also shown in FIG. 8 is a guide member 103 which is adapted to be detachably mounted to head portion 73A of bar 73. Thus, as illustrated, head portion 73A includes slots 73B and C on opposite side edges. Guide 103 includes downwardly projecting leg members 103A and 103B which are spaced apart and are adapted to slidably engage slots 73B and C. The assembled version is illustrated in FIG. 9 (side view).

Figure 13A:
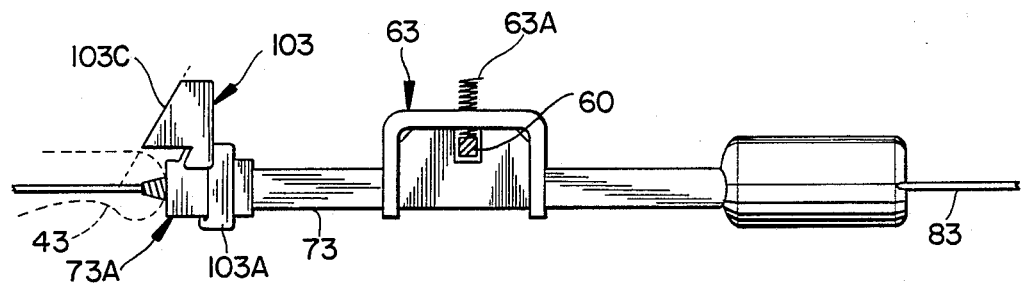
FIG. 13A is a side elevational view illustrating one manner in which the instrumentation of the invention is used to resect the head of a metacarpal bone for implantation of a prosthetic device.

Guide member 103 also includes a sloped planar front face 103C which is useful as a guide in defining the location and orientation of resection of the head of a metacarpal bone 43. This is illustrated in the side elevational view of FIG. 13A. The face 103C may be sloped at an angle of about 30°, for example, with respect to vertical. Other angles could also be used.

Figure 13B:
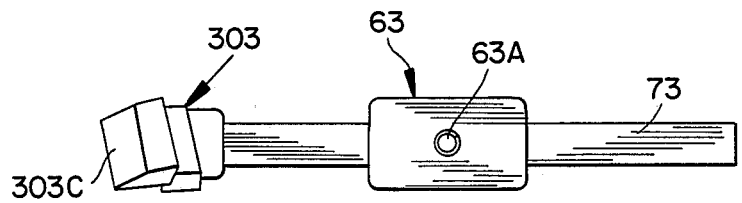
FIG. 13B is a top view of another embodiment of orientation head member defining the plane for resection of a metacarpal head.

FIG. 13B is a top view illustrating another embodiment of orientation head 303 member defining the plane for resection of a metacarpal head. The head 303 includes a front face 303C which is sloped at an angle from vertical and which is also oriented at an angle with respect to the longitudinal axis of the bar 73.

Figures 14A, 14B, 14C:
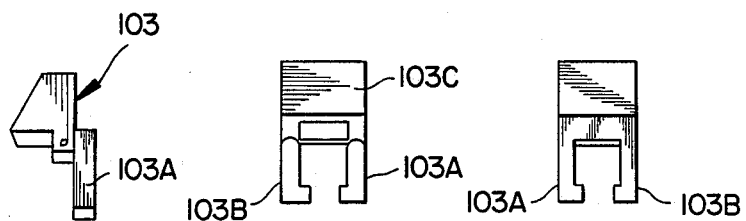
FIGS. 14A, B and C are side elevational, front elevational, and rear elevational views, respectively, of an orientation head member which is useful in the instrumentation of the invention to define the plane used for resection of the metacarpal head.

FIG. 14 illustrates a guide member 103 from different sides. FIG. 14A is a side view; FIG. 14B is a front view; and FIG. 14C is a rear view. Preferably the lower end of each leg includes an inwardly projecting tab (as shown in FIGS. 14B and C) to retain the guide member on head portion 73A.

Another variation is illustrated in FIG. 13C. In this variation the legs 403A of the orientation head 403 are parallel to the face 403C of the head. The slots 173B in the outer end of bar 173 are also sloped in a plane parallel to the face 403C, as illustrated. This arrangement enables the orientation head 403 to be easily slipped onto the end of bar 173 and removed again by moving head 403 along a plane parallel to the face 403C. This allows face 403C to remain in the same plane at all times.

The guide members used on the other elongated bars for the other metacarpal bones are similar to that shown in FIGS. 8, 9, 13 and 14 except that the angle and orientation of the face portion of the guide member will be different for each metacarpal bone. That is, the orientations of the face portions of the guide members on the elongated bars associated with the long and ring finger metacarpals are of equal angular magnitude but are oriented in opposite directions from the mid-line of the hand. Also, the orientations of the face portions of the guide members on the elongated bars associated with the index and little finger metacarpals are of equal angular magnitude but are oriented in opposite directions from the mid-line of the hand.

Also shown in FIG. 8 are K-wire 83, sleeve member 83A, and tool 88. The sleeve member is adapted to be slidably received in the longitudinal bore in bar 73, and the K-wire is adapted to slidably engage a longitudinal bore in the sleeve. Tool 88 includes shank portion 88A having a threaded cutting end portion 88C. Handle 88B is secured to the opposite end.

Figure 12:
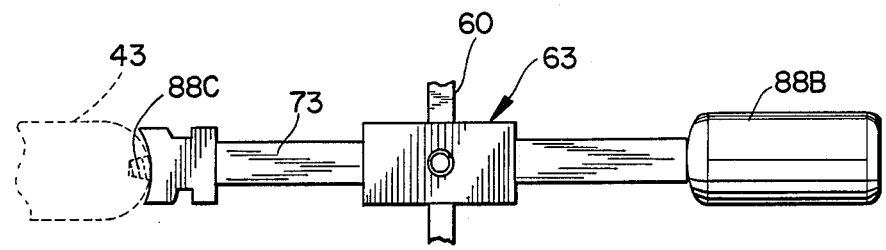
FIG. 12 is a top view illustrating the manner in which the instrumentation of the invention may be secured to the head of a metacarpal bone to be resected.

Tool 88 includes a longitudinal bore therethrough in which a K-wire may be slidably received. This is illustrated in FIG. 11. Tool 88 may also be slidably received in the longitudinal bore through bar 73. This is illustrated in FIG. 12. In this manner the end 88C of tool 88 may cut into and threadably engage the head of a metacarpal bone 43 to securely fasten bar 73 to the bone preparatory to resection thereof in the manner illustrated in FIG. 13. This enables the metacarpal bone 43 to be held securely against the head portion of elongated bar 73.

Figure 16:
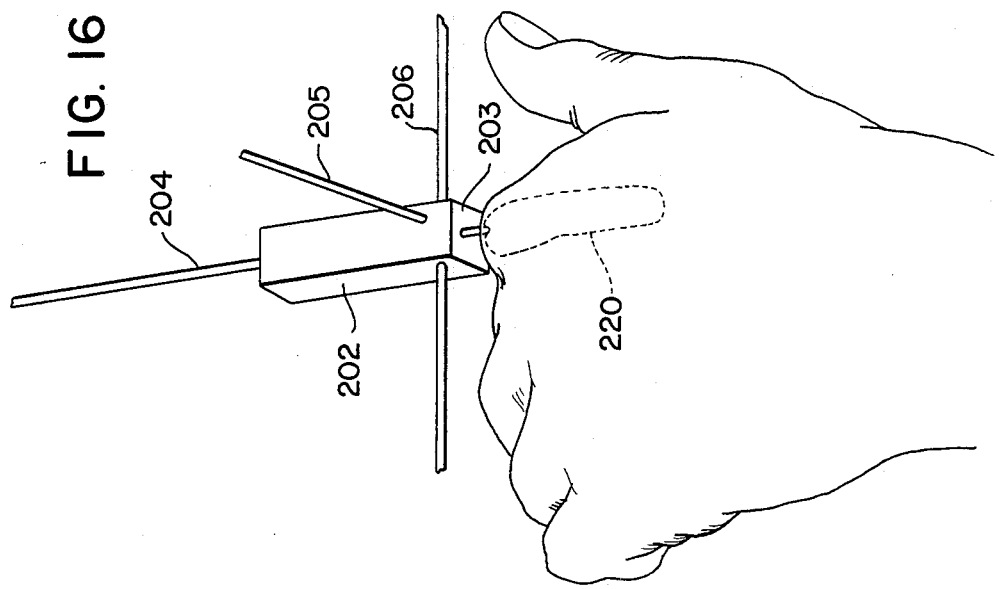
FIGS. 16 and 17 illustrate the manner in which the instrumentation of FIG. 15 is used in this invention.
Figure 17:
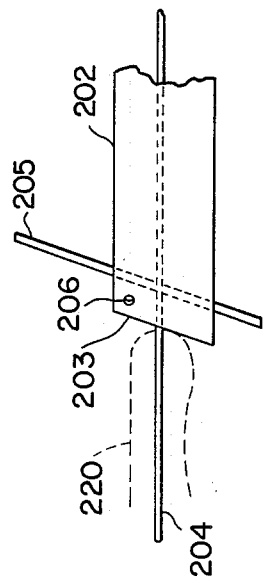
Figure 15:
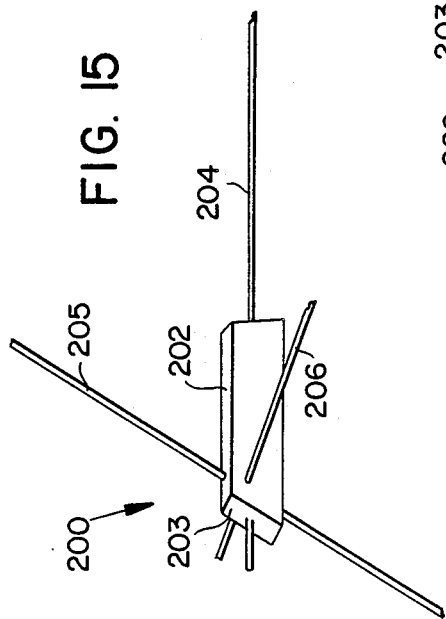
FIG. 15 is a perspective view illustrating another type of instrumentation which is useful in this invention.

FIGS. 15, 16 and 17 illustrate another embodiment of instrumentation which is useful in the practice of the present invention. Thus, there is shown a jig 200 comprising an elongated block or body member 202 having a longitudinal bore therethrough in which a K-wire 204 is slidably received. The K-wire is movable longitudinally.

The K-wire 204 may be inserted into a metacarpal bone 220 along the central axis of the bone, as illustrated in FIG. 17. K-wire 205 passes through a bore in body 202 which is parallel to face 203 in an upright position. K-wire 206 passes through a transverse bore in body 202 which is parallel to face 203, as illustrated. K-wires 205 and 206 are used to assist in orienting face 203 of body 202 relative to metacarpal bone 220.

Figure 18:
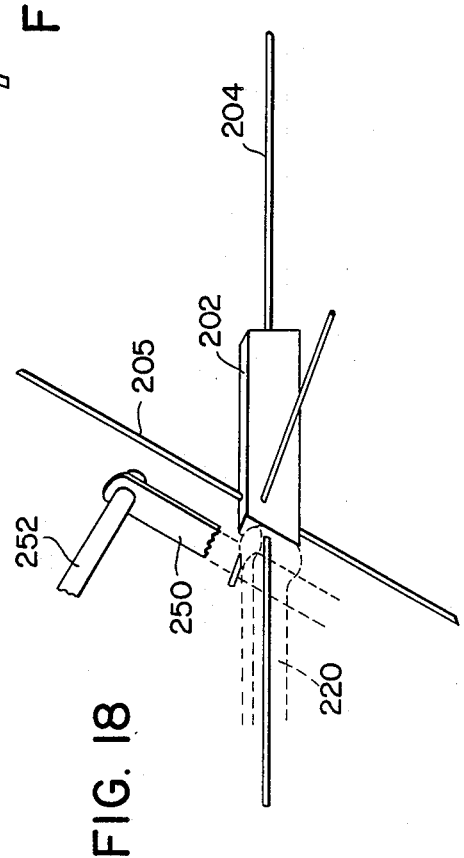
FIG. 18 illustrates one manner in which the head of a metacarpal bone is resected using the instrumentation of FIG. 15.

The front face 203 of body 202 is a sloped planar face. The angle and orientation of the sloped face 203 is predetermined with respect to the longitudinal axis of the body 202. The face 203 serves as a guide for a saw or cutting device used to resect the head of bone 220. This is illustrated in FIG. 18 where oscillating cutting blade 250 (powered by oscillating rod 252) moves downwardly parallel to face 203 of body member 202 to resect the head of metacarpal bone 220.

The angle of face 203 relative to the longitudinal axis of body 202 is in the range of about 20° to 40° amd is preferably about 30°, although other angles could be useful also.

The instrumentation of the invention is extremely useful in enabling the surgeon to control the proper orientation of one or more prosthetic MP joints which are intended for implantation in a metacarpal bone. Other variants are possible without departing from the scope of the present invention.

What is claimed is:

1. Instrumentation for determining and controlling proper orientation of a prosthetic device intended for implantation in a bone of a patient, wherein said device includes an elongated stem member, said instrumentation comprising:
   (a) a transverse support member;
   (b) a mounting block carried on said support member; said mounting block being movably adjustable on said support member;
   (c) an elongated bar carried by said mounting block, said bar being movably adjustable on said mounting block; wherein said bar includes a longitudinal bore therethrough; wherein said bar further includes a head portion at one end thereof;
   (d) a rod member slidably received in said longitudinal bore and being longitudinally movable therein; and
   (e) orientation means carried by said head portion for defining a surface to be cut in said bone.

2. Instrumentation in accordance with claim 1, wherein there are a plurality of said mounting blocks carried on said support member.

3. Instrumentation in accordance with claim 1, wherein said rod member comprises a K-wire.

4. Instrumentation in accordance with claim 2, wherein said prosthetic device is a metacarpophalangeal joint.

5. Instrumentation in accordance with claim 2, wherein said elongated bar carried by each said mounting block further comprises an elongated sleeve member which is slidably received in said longitudinal bore and is removable therefrom.

6. Instrumentation in accordance with claim 2, wherein said orientation means is detachably mounted to said head portion of said elongated bar.

7. Instrumentation in accordance with claim 6, wherein said orientation means comprises a sloped planar surface.

8. Instrumentation in accordance with claim 2, wherein each said elongated bar is mounted to said support member at a predetermined angle.

9. Instrumentation in accordance with claim 2, further comprising frame means for retaining said support member.

10. Instrumentation in accordance with claim 9, wherein said frame means is carried by an x-ray viewer comprising a light source and a viewing surface for supporting an x-ray film showing said bone.

11. Instrumentation in accordance with claim 10, wherein said transverse support member includes first and second ends having openings therein, wherein said frame means includes upstanding posts on opposite sides thereof, and wherein said openings in said ends of said support member are adapted to engage said posts.

12. Instrumentation in accordance with claim 11, wherein said opening in said first end of said support member is circular and said opening in said second end of said support member is slotted.

13. Instrumentation in accordance with claim 2, wherein there are four said mounting blocks, each of which carries a said elongated bar, wherein the first and fourth of said bars form an angle of 11° with respect to a line perpendicular to said transverse support member, and wherein said second and third of said bars form an angle of 4° with respect to said line.

14. Instrumentation in accordance with claim 2, wherein there are four said mounting blocks, each of which carries a said elongated bar; wherein the first and fourth of said bars form equal first angles with respect to a line perpendicular to said transverse support member, wherein the second and third of said bars form equal second angles with respect to said line; wherein said orientation means on said first and fourth bars define equal left and right first angles of cut, respectively; and wherein said orientation means on said second and third bars define equal left and right second angles of cut, respectively.

15. A process for preparing a metacarpal head of a metacarpal bone for implantation of a joint prosthesis having a stem member thereon, said process comprising the steps of:
   (a) providing instrumentation described in claim 1;
   (b) providing an x-ray viewer including a viewing surface for supporting an x-ray film and frame means for retaining said transverse support member;
   (c) placing an x-ray film of a hand on said viewing surface;
   (d) aligning said head portion of said elongated bar with said metacarpal head of said metacarpal bone;
   (e) securing said elongated bar and said mounting block to said transverse support member;

(f) selecting the desired prosthesis intended for implantation;

(g) preparing said hand for implantation of said prosthesis;

(h) aligning said elongated bar with said metacarpal bone; and (i) cutting said metacarpal head in a plane defined by said orientation means.

16. A process in accordance with claim 15, wherein the metacarpal heads of a plurality of metacarpal bones are prepared for implantation of a joint prosthesis in each said bone, wherein there are a plurality of said elongated bars attached to said transverse support member by a plurality of said mounting blocks, wherein each said elongated bar is aligned with a said metacarpal bone on said x-ray film and then secured in position to said support member.

17. A process in accordance with claim 15, wherein said elongated bar carried by each said mounting block further comprises an elongated sleeve member which is slidably received in said longitudinal bore and is removable therefrom; and wherein said orientation means is detachably mounted to said head portion of said elongated bar.

18. A process in accordance with claim 15, wherein each said elongated bar is mounted to said support member at a predetermined angle.

19. A process in accordance with claim 15, wherein said transverse support member includes first and second ends having openings therein, wherein said frame means includes upstanding posts on opposite sides thereof, and wherein said openings in said ends of said support member are adapted to engage said posts.

20. A jig for facilitating orientation and implantation of a prosthesis in a metacarpophalangeal joint, said jig comprising:

(a) an elongated body member including a planar front face which is sloped in a manner such that it forms an angle in the range of about 20° to 40° relative to the longitudinal axis of said body member; wherein said body member further includes a longitudinal aperture therethrough parallel to said longitudinal axis;

(b) an elongated rod member slidably received in said longitudinal aperture and being longitudinally movable therein; and (c) horizontal orientation means carried by said body member for facilitating horizontal orientation thereof.

21. A jig in accordance with claim 20, wherein said rod member comprises a K-wire.

22. A jig in accordance with claim 20, wherein said body member further includes a transverse bore therethrough adjacent said front face and parallel thereto, and wherein said horizontal orientation means comrises a K-wire slidably received in said transverse bore.

23. A jig in accordance with claim 20, wherein said body member includes a vertical bore therethrough adjacent said front face and parallel thereto, and further comprising a K-wire slidably received in said vertical bore.

24. A jig in accordance with claim 20, wherein said front face forms an angle of about 30° relative to said longitudinal axis.

25. A process for preparing a metacarpal head of a metacarpal bone for implantation of a joint prosthesis having a stem member thereon, said process comprising the steps of:

(a) providing a jig described in claim 20;

(b) aligning said rod member with the central axis of said metacarpal bone;

(c) inserting said rod member through said metacarpal head and into said bone;

(d) sliding said body member along said rod member to position said front face adjacent to said metacarpal head;

(e) orienting said front face using said horizontal orientation means;

(f) cutting through said metacarpal head in a plane parallel to said front face.

26. Instrumentation for determining and controlling proper orientation of a plurality of prosthetic devices, wherein each said device is intended for implantation in a bone of a patient, wherein each said device includes an elongated stem member, said instrumentation comprising:

(a) transverse support means;

(b) a plurality of elongated bars carried by said support means; each said bar being movably adjustable on said support means; and (c) orientation means supported by said bars for defining a surface to be cut in each said bone.

* * * * *